United States Patent [19]

Miki et al.

[11] 4,025,644
[45] May 24, 1977

[54] TYROSINE DERIVATIVES AND USE

[75] Inventors: Tosaku Miki; Yasuhiro Hosokawa; Tamotsu Miwa; Hiroshi Fujita; Masahide Asano; Shunzo Aibara, all of Tokyo, Japan

[73] Assignee: Daiichi Seiyaku Co., Ltd., Tokyo, Japan

[22] Filed: Dec. 9, 1975

[21] Appl. No.: 639,117

[30] Foreign Application Priority Data

| Dec. 18, 1974 | Japan | 49-145133 |
| Dec. 18, 1974 | Japan | 49-145134 |
| Apr. 2, 1975 | Japan | 50-39959 |
| Apr. 4, 1975 | Japan | 50-41000 |

[52] U.S. Cl. .................. 424/300; 260/471 C; 260/519; 260/557 R; 260/558 A; 260/558 D; 260/558 P; 260/559 R; 260/559 S; 260/559 A; 424/319; 424/324

[51] Int. Cl.² .......................................... C07C 125/06

[58] Field of Search ............... 260/471 C; 424/300

[56] References Cited

UNITED STATES PATENTS

| 3,843,796 | 10/1974 | Miller | 260/471 C X |
| 3,846,476 | 11/1974 | Kaiser et al. | 260/471 C |

FOREIGN PATENTS OR APPLICATIONS

| 1,158,493 | 12/1963 | Germany | 260/471 C |
| 88,278 | 9/1956 | Norway | 260/471 C |

OTHER PUBLICATIONS

Santi et al., Journal of Medicinal Chemistry, vol. 16, No. 3 (1973) pp. 273–280.

*Primary Examiner*—Richard L. Raymond
*Attorney, Agent, or Firm*—Oblon, Fisher, Spivak, McClelland & Maier

[57] ABSTRACT

Compounds having the formula:

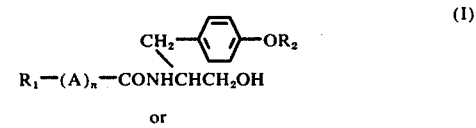

or

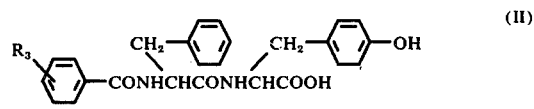

wherein $R_1$ is phenyl or cycloalkyl and the phenyl may have at least one substituent selected from the group consisting of lower alkyl, lower alkoxy, amino and nitro; $R_2$ is hydrogen or lower alkyl; A is $-CH_2O-$ or $-CH_2CH(O\text{-lower alkyl})-$; $n$ is zero or 1 when $R_1$ together with $(A)_n$ is unsubstituted phenyl, $R_2$ is lower alkyl; and $R_3$ is hydrogen or lower alkoxy, have antiulcerousaction.

5 Claims, No Drawings

TYROSINE DERIVATIVES AND USE

BACKGROUND OF THE INVENTION

1. Field of the Invention

The present invention relates to novel tyrosine derivatives which have anti-ulcerous action.

2. SUMMARY OF THE INVENTION

The novel derivatives of this invention have the following general formulas:

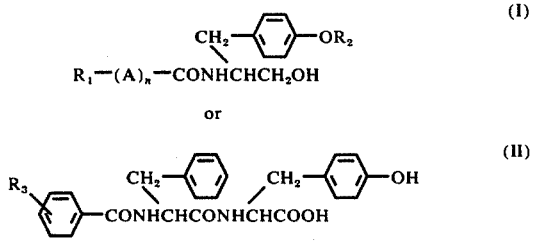

wherein $R_1$ is phenyl or a cycloalkyl such as cyclopentane, cyclohexane or cycloheptane, and the phenyl may have one or more substituents such as lower ($C_1$–$C_6$) alkyl, lower ($C_1$–$C_6$) alkoxy, halogen (F, Cl, Br or I), amino or nitro; $R_2$ is hydrogen or lower ($C_1$–$C_6$) alkyl; A is —$CH_2O$— or

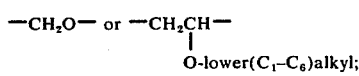

$n$ is zero or 1; when $R_1$ together with $(A)_n$ is unsubstituted phenyl, $R_2$ is lower ($C_1$–$C_6$) alkyl and $R_3$ is hydrogen or lower ($C_1$–$C_6$) alkoxy.

DETAILED DESCRIPTION OF THE PREFERRED EMBODIMENTS

The compound of formula (I) is a tyrosinol derivative and the compound of formula (II) is a phenylalanyl-tyrosine derivative. Herein, both classes of compounds are regarded as tyrosine derivatives. Furthermore, both show remarkable anti-ulcerous effects, especially against chronic gastric ulcers.

Compound (I) can be synthesized by various reactions know per se, such as reduction of the corresponding carboxylic acid, ester or aldehyde, or acylation of tyrosinol or O-methyl-tyrosinol. Likewise, compound (II) can be synthesized by acylation of phenylalanyl-tyrosine, condensation or N-acylphenylalanine with tyrosine ester, and like processes. These syntheses are summarized as follows:

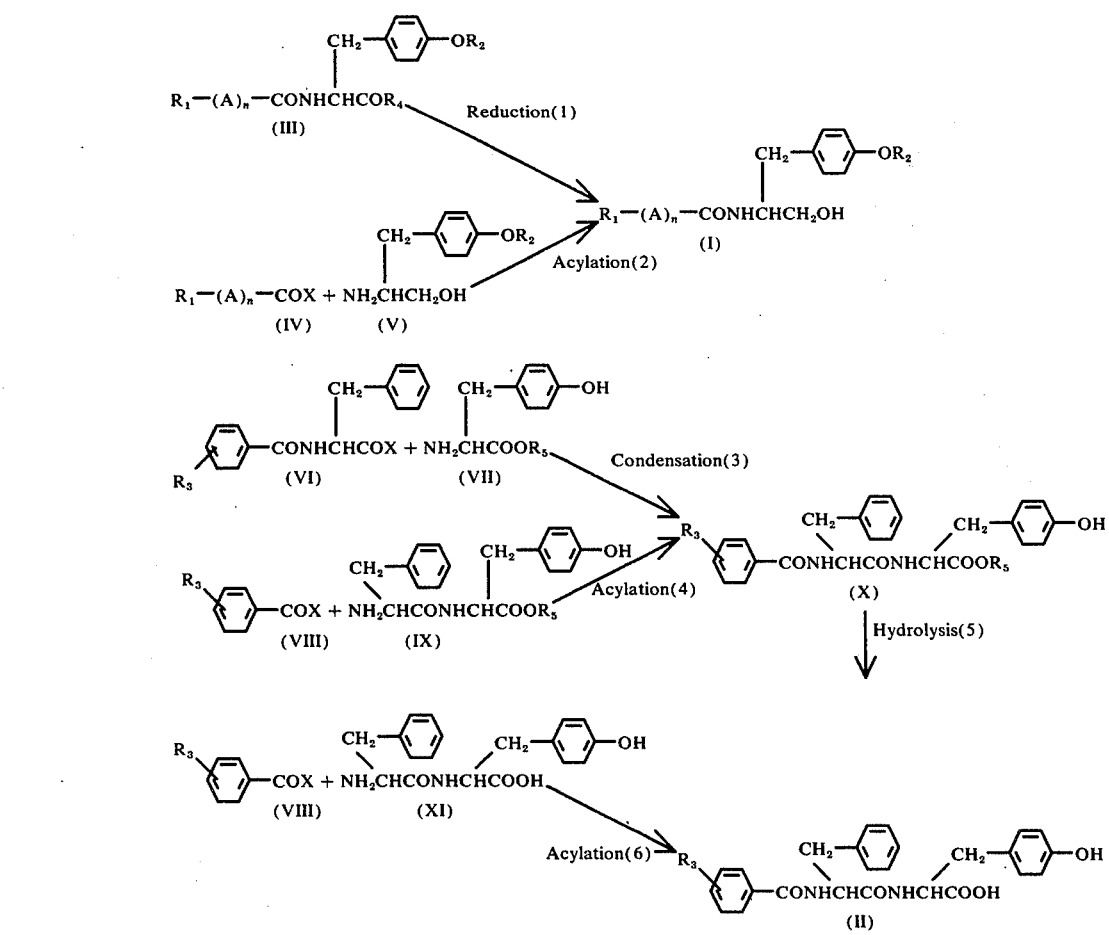

$R_1$, $R_2$, $R_3$, A and $n$ are the same as above and $R_4$ is H, OH or alkoxy; $R_5$ is alkyl and X forms a carboxyl group or forms a functional group of the carboxyl group together with —CO, e.g. X can be hydroxy or halogen or forms an acid anhydride or ester, and the like.

Reductive reaction (I) is conducted by contacting compound (III) with a suitable reducing agent in an inert solvent. Suitable reducing agents include metal hydride complexes such as sodium borohydride, lithium borohydride or lithium aluminum hydride, organometallic hydride complexes such as sodium dihydro-bis-(2-methoxyethoxy)-aluminate, or diborane and the like. Sodium borohydride is preferred since then the reaction can be carried out in an alcohol or an aqueous alcohol. Optional addition of various halogen compounds such as aluminum chloride, calcium chloride or boron trifluoride is helpful in some cases. Suitable solvents which may be used as the reaction medium include ethers such as ethyl ether, tetrahydrofuran, dioxane or diethyleneglycoldimethylether; aromatic hydrocarbons such as benzene and the like; and pyridine. This reaction generally proceeds at room temperature. However, it may be carried out while cooling or heating if desired.

When $R_4$ is OH in formula (III), the compound is preferably made by first reacting with an ester of chlorocarbonic acid and then with a reducing agent. That is, compound (III) is mixed with a chlorocarbonic ester such as the methyl, ethyl, n-propyl or isobutyl ester to react with it at a temperature of from $-10°$ C to $-15°$ C in the presence of tertiary amines such as trimethyl amine, trimethylamine, pyridine, and the like. Then the product is reduced as above to yield compound (I).

Compound (I) can be prepared through acylation as well. Acylation reaction (2) may be carried out by contacting tyrosinol or O-alkyltyrosinol (V) with compound (IV) (functional derivatives or carboxylic acids, such as acid halides) in a suitable solvent. The reaction proceeds advantageously in the presence of acid-acceptors such as alkali metal hydroxides, carbonates, or bicarbonates; or tertiary amines such as triethylamine, trimethylamine, pyridine, and the like. The reaction temperature can be suitably selected in accordance with the reactants, for example, at room temperature, at elevated temperature, or by cooling. Suitable solvents, include water, alcohols such as methanol or ethanol, acetic esters, chloroform, benzene. Aqueous solvents are preferred. The desired compound (I) can be isolated and purified by conventional methods such as extraction, chromatography, recrystallization and the like.

In order to prepare compound (II), several schemes may be employed. These processes consist of condensation, acylation and hydrolysis, and are summarized above. The acylations (4) and (6) may be carried out in a similar manner to those of acylation (2). Condensation reaction (3) may be conducted by reacting compound (VI) (for example X=OH) with compound (VII) in the presence of a suitable condensing agent such as dicyclohexyl-carbodiimide, 1-ethyl-3-(3-methylaminopropyl) carbodiimide or diphenylphosphorylazide. Alternatively, the condensation may be performed by reacting compound (VI) (for example, an acid halide, an active ester, or a mixed acid anhydride) with compound (VII) in the presence of a suitable acid-acceptor. These condensation reactions can be carried out at room temperatures, but, as noted above, may proceed at elevated temperature or with cooling, if desired. Suitable solvents which may be used as the reaction medium include chloroform, dimethylformamide, tetrahydrofuran, ethyl acetate and the like. Suitable acid-acceptors include alkali metal hydroxides such as sodium hydroxide or potassium hydroxide, alkali metal carbonates such as sodium or potassium carbonate, organic tertiary amines such as triethylamine, trimethylamine or pyridine, and the like. The hydrolysis reaction (5) can be performed by conventional methods, e.g., compound (X) can be hydrolysed in the presence of an acid or base at room temperature, elevated temperature or with cooling. The desired product (II) can be isolated and purified in the usual manner such as by extraction, chromatography, recrystallization and the like. The compound is normally obtained as a free acid. However, it can be obtained as a salt of any alkali metal such as sodium, potassium or lithium; an alkaline earth metal such as calcium, magnesium; aluminum and the like.

Those starting materials which are novel compounds can be prepared using known reactions as are illustrated in the Examples.

The anit-ulcerous effects of the object compounds of this invention have been confirmed in tests on ulcers in rats. The ulcers were produced according to the method of K. Takagi, S. Okabe and R. Saziki, by the effect of acetic acid on the digestive organs (Japanese Journal of Pharmacology vol. 19 pages 418–426 (1969), Yakkyoku vol. 25 pages 1453–1459 (1974) and Experientia vol. 27 pages 146–148 (1971). It is known that this experimental ulcer resembles human peptic ulcers with respect to the overall and histological findings and as to the recovery process. The experimental details confirming the anti-ulcerous effect are as follows.

Donryu-strain male rats having a body weight — 230–270g (10 rats to a group) were not fed for 24 hours and then were anesthesized with ether. A laparotomy was performed. The stomach was exposed and 0.05 ml of 10% acetic acid was injected into the subserosal layer in the glandular part of the anterior wall to produce the experimental ulcers. The abdomen was then closed. Beginning on the day after the ulceration, the compounds of this invention were orally administered to the rats for 13 days. The rats were fed normally and sacrified on the 15th day after the ulcer formation. The size of the ulcer (length and width) in the glandular part of the stomach was measured and the product of the length and width was used as the ulcer index (UI). The curative ratio (%) was calculated from the ulcer index of the rats which were medicated as compared with the index of the control group.

$$\text{Curative ratio (\%)} = \frac{UI_{control} - UI_{medicated}}{UI_{control}} \times 100$$

For the purpose of comparing the effects with those of known drugs, the therapeutic effects of the compounds of this invention, tyrosine itself and gefarnate relative to those of glutamine were calculated and are listed in Table I. Of these compounds, gefarnate (geranyl farnesylacetate, U.S. Pat. No. 3,154,570 (1964) and glutamine are known anti-ulcerous drugs.

Acetic acid ulcers in rats are known to undergo partial healing and re-ulceration so that these ulcers resemble human chronic ulcers, both histologically and functionally.

In order to examine the anti-ulcerous effects on chronic ulcers, the compounds of this invention were orally administered to rats for 14 days, from the 41st day to the 54th day after ulceration with acetic acid. On the 55th day, the rats were sacrificed and the size of the ulcer was measured. The therapeutic effects relative to glutamine effects were calculated and are listed in Table II. The procedure used in ulceration and in the determination of effects are the same as those described hereinbefore.

As can be seen from the data in Tables I and II, the tyrosine derivatives of this invention display remarkable effects against gastric ulcers, and especially regarding experimental chronic ulcers are surprisingly superior to known drugs for treating these ulcers in humans.

When the tyrosine derivatives are used in humans for prevention or treatment of gastric ulcers, the daily oral dosage should normally be within the range of 200 to 1200mg/man, preferably 400 to 800mg/man.

As for acute toxicity, the $LD_{50}$'s for the tyrosine derivatives of this invention were found to be over 4g/kg body weight in mice, as can be seen from Table I, and over 2g/kg body weight in rats, when orally administered.

TABLE II-continued

| Compound | Dose mg/kg/day | Relative therapeutic effect |
|---|---|---|
| $R_3=CH_3O$ | 50 | 7.85 |
| Glutamine | 1000 | 1.00 |
| Gefarnate | 200 | 0.77 |

Having generally described the invention, a more complete understanding can be obtained by reference to certain specific examples, which are included for purposes of illustration only and are not intended to be limiting unless otherwise specified.

In the examples all aminoacids and dipeptides are in their optically active L-forms or are prepared therefrom, unless otherwise specified.

TABLE I

| Compound | | | | Dose mg/kg/day | Relative therapeutic effect | $LD_{50}$ g/kg body weight (mouse p.o.) |
|---|---|---|---|---|---|---|
| $R_1$ | $R_2$ | n | A | | | |
| Compound I: $CH_3O$—⌬— | H | 0 | — | 200 | 1.76 | >4 |
| $OCH_3$ / ⌬— | H | 0 | — | 200 | 1.29 | |
| $CH_3O$ \ , $CH_3O$—⌬— | H | 0 | — | 200 | 1.43 | >4 |
| $CH_3O$ \ , $NH_2$—⌬— | H | 0 | — | 200 | 1.24 | |
| ⌬— | $CH_3$ | 1 | $-CH_2O-$ | 200 | 1.03 | >4 |
| $CH_3$—⌬— | H | 1 | $-CH_2O-$ | 200 | 1.81 | >4 |
| $CH_3O$—⌬— | H | 1 | $-CH_2O-$ | 200 | 1.75 | >4 |
| $CH_3O$ \ , $CH_3O$—⌬— | $CH_3$ | 1 | $-CH_2O-$ | 200 | 0.98 | >4 |
| F—⌬— | H | 1 | $-CH_2O-$ | 200 | 1.14 | |
| Cl—⌬— | H | 1 | $-CH_2O-$ | 200 | 0.81 | |
| ⟨H⟩— | H | 1 | $-CH_2O-$ | 200 | 1.60 | |
| ⌬ | H | 1 | $-CH_2CH-OCH_3$ | 200 | 1.01 | >4 |
| Compound (II) | $R_3=H$ | | | 200 | 1.19 | >4 |
| | $R_3=CH_3O$ | | | 200 | 1.75 | >4 |
| Glutamine | | | | 200 | 0.30 | |
| | | | | 1000 | 1.00 | |
| Gefarnate | | | | 200 | 1.06 | |
| Tyrosine | | | | 200 | 0.37 | |

TABLE II

| Compound | Dose mg/kg/day | Relative therapeutic effect |
|---|---|---|
| Compound (I) $R_1=CH_3O$—⌬—, $R_2=H$, n=1, $A=-CH_2O-$ | 50 | 7.72 |
| Compound (II) | | |

EXAMPLE 1

In 30 ml of tetrahydrofuran, 3.2 g of N-(cyclohexyl-methoxy-carbonyl)-tyrosine was dissolved. To the solution were added 1.1 g of ethyl chlorocarbonate and 1.0 g of triethylamine while cooling with ice and stirring. After stirring the mixture for 10 minutes, the precipitate was removed by filtration. The filtrate was added to a suspension of 1.0 g of sodium borohydride and 10 ml of tetrahydrofuran cooled with ice. The mixture was stirred for 2 hours, then neutralized with hydrochloric acid and concentrated in vacuo. The residue was extracted with ethyl acetate and the extract was washed with water, dried and concentrated to dryness. The residue was crystallized from ethyl acetate-petroleum ether to give 2.3 g of N-(cyclohexylmethylcarbonyl)-tyrosinol with a melting point of 121°–126° C.

Analysis calculated for $C_{17}H_{25}O_4N$: C,66.43: H, 8.20; N, 4.56; showed C, 66.65, H, 8.11; N, 4.32.

EXAMPLE 2

In 20 ml of tetrahydrofuran, 574 mg of lithium aluminium hydride was suspended. To the suspension was added dropwise 20 ml of tetrahydrafuran solution containing 1.0 g of N-(cyclohexylmethoxy-carbonyl)-tyrosine while stirring and cooling with ice. The mixture was stirred at room temperature for 2 hours. After addition of 5% hydrochloric acid, the mixture was concentrated in vacuo and extracted with ethyl acetate. The extract was washed with water, dried and concentrated to dryness. The residue was dissolved in chloroform and subjected to column chormatography with 10 g of silicagel to give 322 mg of N-(cyclohexylmethoxycarbonyl)-tyrosinol.

EXAMPLE 3

In 20 ml of tetrahydrofuran was dissolved 10 ml of a 65% toluene solution of sodium dihydrobis-(2-methoxyethoxy)-aluminate. To the solution was added dropwise 20 ml of tetrahydrofuran solution and 1.0 g of N-(cyclohexylmethoxycarbonyl)-tyrosine while stirring and cooling with ice. The mixture was stirred at room temperature for 2 hours. After addition of 5% hydrochloric acid, the mixture was extracted with ethyl acetate. The extract was washed with water, dried and concentrated. The residue was crystallized from ethyl acetate-petroleum ether to give 410 mg of N-(cyclohexylmethoxycarbonyl)-tyrosinol.

EXAMPLE 4

In 50 ml of tetrahydrofuran was dissolved 1.0 g of N-(cyclohexylmethoxycarbonyl)-tyrosine. To the solution, 380 mg of sodium borohydride was added with stirring. After 10 minutes, to the mixture was added dropwise 15 ml of tetrahydrofuran solution containing 1.45 ml of boron trifluoride etherate. The mixture was stirred for 20 hours. After addition of 3% hydrochloric acid, the mixture was concentrated and extracted with ethyl acetate. The extract was washed with water, dried and concentrated to dryness. The residue was dissolved in chloroform and subjected to column chromatography with 10 g of silicagel to give N-(cyclohexylmethoxy-carbonyl) tyrosinol.

EXAMPLE 5

In 15 ml of diglyme (bis (2-methoxyethyl) ether) was dissolved 1.0 g of N-(cyclohexylmethoxycarbonyl)-tyrosine. To the solution were added 570 mg of sodium borohydride and 50 ml of diglyme solution containing 7g of anhydrous aluminum chyloride. The mixture was stirred at room temperature for 2 hours. After addition of 150 ml of water, the reaction mixture was concentrated in vacuo and the residue was extracted with ethyl acetate. The extract was washed with water, dried and concentrated to dryness. The residue was crystallized from ethyl acetate-petroleum ether to give N-(cyclohexylmethoxycarbonyl)-tyrosinol.

According to the same procedure as used in Example 1, the following tyrosinol drivatives were prepared from the corresponding acyl tyrosines.

EXAMPLE 6

N-(4-methoxybenzoyl)-tyrosinol: yield 55% mp. 181°–183° C. Analysis, calculated for $C_{17}H_{19}O_4N$: C, 67.76; H,6.36; N,4.65; found C,67.44; H,6.51; N,4.73.

EXAMPLE 7

N-(2-methoxybenzoyl)-tyrosinol: yield 70%; mp. 121°–122° C. Analysis, calculated for $C_{17}H_{19}O_4N$; C,67.75; H,6.36; N,4.65, found C,67.89; H, 6.24; N,4.81.

EXAMPLE 8

N-(3,4,5-trimethoxybenzoyl)-tyrosinol: yield 61%; mp. 112°–114° C. Analysis, calculated for $C_{19}H_{23}O_6N$: C,63.14; H,6.42; N,3.88; found C,63.24; H,6.54; N,4.01.

EXAMPLE 9

N-(4-chlorobenzoyl)-tyrosinol: yield 74%, mp. 183°–184° C. Analysis, calculated for $C_{16}H_{16}O_3NCl$: C,62.85; H,5.27; N,4.58; found C,62.92; H,5.14; N,4.63.

EXAMPLE 10

N-(2-chlorobenzoyl)-tyrosinol: yield 82% amorphous powder. Analysis, calculated for $C_{16}H_{16}O_3NCl$: C,62.85; H,5.27; N,4.58; found C, 62.54; H,5.53; N,4.67.

EXAMPLE 11

N-(4-aminobenzoyl)-tyrosinol: yield 45%; mp. 174°–177° C. Analysis, calculated for $C_{16}H_{18}O_3N_2$: C,67.11; N,6.34; N,9.78; found C,67.58; H,6.20; N,9.38.

EXAMPLE 12

O-methyl-N-benzyloxycarbonyltyrosinol: yield 68%; mp. 99°–100° C. Analysis, calculated for $C_{18}H_{21}O_4N$: C,68.55; H,6.71; N,4.44; found C,68.40; H,6.42; N,4.59.

EXAMPLE 13

N-(4-methylbenzyloxycarbonyl)-tyrosinol: yield 68%; mp. 128°–129° C. Analysis, calculated for $C_{18}H_{21}O_4N$: C,68.55; H,6.72; N,4.44; found C, 68.42; H,6.54; N,4.71.

EXAMPLE 14

N-(2-methylbenzyloxycarbonyl)-tyrosinol: yield 60%; mp. 78°–81° C. Analysis, calculated for $C_{18}H_{21}O_4N$: C,68.55; H,6.72; N,4.44; found C,68.72; H,6.53; N,4.12.

EXAMPLE 15

N-(4-methoxybenzyloxycarbonyl)-tyrosinol: yield 68%; mp. 139°–141° C. Analysis, calculated for $C_{18}H_{21}O_5N$: C,65.24; H,6.39; N,4.23; found C, 65.31; H,6.11; N,4.47. $[\alpha]_D^{22}$ − 41.9° (methanol).

EXAMPLE 16

O-methyl-N-(3,4-dimethoxybenzyloxycarbonyl)-tyrosinol: yield 70%; mp. 97°–98° C. Analysis, calculated for $C_{20}H_{25}O_6N$: C,63.98; H,6.71; N,3.73; found C,63.72; H,6.94; N,3.53.

EXAMPLE 17

N-(4-fluorobenzyloxycarbonyl)-tyrosinol: yield 61%; mp. 114°–116° C. Analysis, calculated for $C_{17}H_{18}O_4NF$: C,63.94; H,5.68; N,4.39; found C,63.61; H,5.24; N,4.58.

EXAMPLE 18

N-(4-chlorobenzyloxycarbonyl)-tyrosinol: yield 78%; mp. 139°–141° C. Analysis, calculated for $C_{17}H_{18}O_4NCl$: C,60.80; H,5.40; N,4.17; found C,60.99; H,5.25; N,4.48.

EXAMPLE 19

N($\alpha$-methoxy-$\beta$-phenylpropionyl)-tyrosinol: yield 65%; mp. 139°–141° C. Analysis, calculated for $C_{19}H_{23}O_4N$: C,69.28; H,7.04; N,4.25; found C,69.01; H,7.41; N,4.05.

EXAMPLE 20

In 150 ml of 50% aqueous methanol, 13.1 g of sodium borohydride was added with stirring while cooling with ice. To the mixture was added dropwise 250 ml of a methanol solution containing 26.5 g of methyl N-(4-methylbenzyloxycarbonyl)-tyrosinate. The mixture was stirred while cooling with ice for 2 hours and at room temperature for four hours. After neutralization with 10% hydrochloric acid, the mixture was concentrated in vacuo and extracted with ethyl acetate. The extract was washed with water, dried and concentrated to dryness. The residue was crystallized from ethyl acetate-petroleum ether to give 17.9 g of N-(4-methylbenzyloxycarbonyl)-tyrosinol: yield 74%; mp. 128°–129° C. Analysis, calculated for $C_{18}H_{21}O_4N$: C,68.55; H,6.72; N,4.44; found C,68.51; H,6.84; N,4.29.

According to the same procedure as used in Example 20, the following tyrosinol derivatives were prepared from the corresponding tyrosine esters.

EXAMPLE 21

N-(4-methoxybenzoyl)-tyrosinol: yield 48%.

EXAMPLE 22

N-(2-methoxybenzoyl)-tyrosinol: yield 76%.

EXAMPLE 23

N-(3,4,5-trimethoxybenzoyl)-tyrosinol: yield 65%.

EXAMPLE 24

N-(4-chlorobenzoyl)-tyrosinol: yield 88%.

EXAMPLE 25

N-(2-chlorobenzoyl)-tyrosinol: yield 91%.

EXAMPLE 26

N-(4-aminobenzoyl)-tyrosinol: yield 60%.

EXAMPLE 27

O-methyl-N-benzyloxycarbonyltyrosinol: yield 80%.

EXAMPLE 28

N-(2-methylbenzyloxycarbonyl)-tyrosinol: yield 50%.

EXAMPLE 29

N-(4-methoxybenzyloxycarbonyl)-tyrosinol: yield 63%.

EXAMPLE 30

O-methyl-N-(3,4-dimethoxybenzyloxycarbonyl)-tyrosinol: yield 76%.

EXAMPLE 31

N-(4-fluorobenzyloxycarbonyl)-tyrosinol: yield 67%.

EXAMPLE 32

N-(4-chlorobenzyloxycarbonyl)-tyrosinol: yield 83%.

EXAMPLE 33

N-(cyclohexylmethoxycarbonyl)-tyrosinol: yield 79%.

EXAMPLE 34

N-($\alpha$-methoxy-$\beta$-phenylpropionyl)-tyrosinol: yield 79%.

EXAMPLE 35

In 30 ml of tetrahydrofuran was dissolved 1.0 g of methyl N-(4-chlorobenzyloxycarbonyl) tyrosinate. To the solution was slowly added 280 mg of sodium aluminium hydride with stirring and the mixture was stirred for 2 hours. After addition of 50 ml of 1N hydrochloric acid, the mixture was concentrated in vacuo. The residue was extracted with ethyl acetate and the extract was washed with water, dried and concentrated to dryness. The residue was crystallized from ethyl acetate-petroleum ether to give 610 mg of N-(4-chlorobenzyloxycarbonyl)-tyrosinol: yield 66%.

EXAMPLE 36

In 30 ml of tetrahydrofuran was dissolved 1.0 g of methyl (N-(4-chlorobenzyloxycarbonyl)-tyrosinate. To the solution was added dropwise 10 ml of tetrahydrofuran solution containing 4.2 ml of sodium dihydro-bis-(2-methoxyethoxy) aluminate (65% toluene solution) with stirring while cooling with ice. The mixture was stirred at room temperature for 1 hour. After addition of 200 ml of 3% hydrochloric acid, the reaction mixture was concentrated in vacuo and extracted with ethyl acetate. The extract was washed with water, dried and concentrated to dryness. The residue was dissolved in chloroform and subjected to column chromatography with 10 g of silicagel to give 509 mg of N-(4-chlorobenzyloxycarbonyl)-tyrosinol: yield 56%.

EXAMPLE 37

According to the same procedure as used in Example 20 N-(4-chlorobenzyloxycarbonyl)-tyrosinol was prepared in a yield of 95%.

EXAMPLE 38

In a mixture of 10 ml of water and 20 ml of ethyl acetate, 1.6 g of tyrosinol was dissolved. To the solution were added dropwise 2 g of 2-methylbenzyloxycarbonyl chloride and 10 ml of an aqueous solution containing 1.3 g of sodium carbonate alternately with stirring while cooling with ice. After stirring for two hours at room temperature, the ethyl acetate layer was collected and washed with 5% hydrochloric acid and then with water. The layer was dried and concentrated to dryness. The residue was crystallized from ethyl acetate-petroleum ether to give 2.2 g of N-(2-methylbenzyloxycarbonyl)-tyrosinol with a mp. 78°–81° C in a yield of 70%. Analysis, calculated for $C_{18}H_{21}O_4N$: C,68.55; H,6.72; N,4.44; found C,68.88; H,6.84; N,4.42.

According to the same procedure as used in Example 38, the following tyrosinol derivatives were prepared from the corresponding chlorides.

EXAMPLE 39

N-(4-methoxybenzoyl)-tyrosinol: yield 54%; mp. 181°–183° C. Analysis, calculated for $C_{17}H_{19}O_4N$: C,67.76; H,6.36; N,4.65; found C,67.43; H,6.54; N,4.81.

EXAMPLE 40

N-(2-methoxybenzoyl)-tyrosinol: yield 62%; mp. 121°–122° C. Analysis, calculated for $C_{17}H_{19}O_4N$: C,67.76; H,6.36; N,4.65; found C,68.60; H,6.58; N,4.38.

EXAMPLE 41

N-(3,4,5-trimethoxybenzoyl)-tyrosinol: yield 50%; mp. 112°–114° C. Analysis, calculated for $C_{19}H_{23}O_6N$: C,63.14; H,6.42; N,3.88; found C,62.89; H,6.31, N,3.98.

EXAMPLE 42

N-(4-chlorobenzoyl)-tyrosinol: yield 72%; mp. 183°–184° C. Analysis, calculated for $C_{16}H_{16}O_3NCl$: C,62.85; H,5.27; N,4.58; found C,62.53; H,5.58; N,4.29.

EXAMPLE 43

N-(2-chlorobenzoyl)-tyrosinol: yield 78% amorphous powder. Analysis, calculated for $C_{16}H_{16}O_3NCl$: C,62.85; H,5.27; N,4.58; found C,63.03; H,5.11; N,4.81.

EXAMPLE 44

N-(4-aminobenzoyl)-tyrosinol: yield 52%; mp. 174°–177° C. Analysis, calculated for $C_{16}H_{18}O_3N_2$: C,67.11; H,6.34; N,9.78; found C,67.45; H,6.01; N,9.52.

EXAMPLE 45

O-methyl-N-benzyloxycarbonyl-tyrosinol: yield 78%; mp. 99°–100° C. Analysis, calculated for $C_{18}H_{21}O_4$: C,68.55; H,6.71; N,4.44; found C,68.21; H,6.91; N,4.30.

EXAMPLE 46

N-(4-methylbenzyloxycarbonyl)-tyrosinol: yield 53%; mp. 128°–129° C. Analysis, calculated for $C_{18}H_{21}O_4N$: C,68.55; H,6.72; N,4.44; found C,68.29; H,6.88; N,4.21.

EXAMPLE 47

N-(4-methoxybenzyloxycarbonyl)-tyrosinol: yield 42%; mp. 139°–141° C. Analysis, calculated for $C_{18}H_{21}O_5N$: C,65.24; H,6.39; 4.23, found C, 65.01; H,6.58; N,4.52 $[\alpha]_D^{22} - 41.9°$ (methanol).

EXAMPLE 48

O-methyl-N-(3,4-dimethoxybenzyloxycarbonyl)-tyrosinol: yield 39%; mp. 97°–98° C. Analysis, calculated for $C_{20}H_{25}O_6N$: C,63.98; H,6.71; N,3.73; found C,63.62; H,6.99; N,3.50.

EXAMPLE 49

N-(4-fluorobenzyloxycarbonyl)-tyrosinol: yield 59%; mp. 114°–116° C. Analysis, calculated for $C_{10}H_{18}O_4NF$: C,63.94; H,5.68; N,4.39; found C,63.68; H,5.91; N,4.43.

EXAMPLE 50

N-(4-chlorobenzyloxycarbonyl)-tyrosinol: yield 66%; m.p. 139°–141° C, Analysis, calculated for $C_{17}H_{18}O_4NCl$: C,60.80; H,5.40; N,4.17; found C,60.55, H,5.62, N,4.01.

EXAMPLE 51

N-(cyclohexylmethoxycarbonyl)-tyrosinol: yield 68%; mp. 121°–126° C. Analysis, calculated for $C_{17}H_{25}O_4N$: C,66.43; H,8.20; N,4.56; found C,66.09; H,8.42; N,4.81.

EXAMPLE 52

N-($\alpha$-methoxy-$\beta$-phenylpropionyl)-tyrosinol: yield 61%; mp. 139°–141° C. Analysis, calculated for $C_{19}H_{23}O_4N$: C,69.28; H,7.04; N,4.25; found C,69.42; H,6.87; N,4.33.

EXAMPLE 53

In 50 ml of methanol, 4.4 g of methyl N-benzoyl-phenylalanyltyrosinate was dissolved. After addition of 23 ml of 1 N sodium hydroxide, the solution was stirred for 1 hour. The reaction mixture was neutralized with hydrochloric acid, concentrated and extracted with ethyl acetate. The extract was washed with water, dried and concentrated to dryness. The residue was crystallized from ethyl acetate to give 3.8 g of N-benzoyl-phenylalanyltyrosine with a mp. 191°–192° C, in a yield of 87%. Analysis, calculated for $C_{25}H_{24}O_5N_2$: C,69.43; H,5.59; N,6.48; found C,68.98; H,5.72; N,6.37.

EXAMPLE 54

In 150 ml of methanol, was dissolved 30 g of methyl N-(4-methoxybenzoyl)-phenylalanyltyrosinate. After addition of 145 ml of 1 N sodium hydroxide, the mixture was stirred at 50° C for 2 hours. The reaction mixture was neutralized with hydrochloric acid, concentrated and extracted with ethyl acetate. The extract was washed with water, dried and concentrated to dryness. The residue was crystallized from ethyl acetate to give 23.9 g of N-(4-methoxybenzoyl)-phenylalanyltyrosine with a mp. 198°–200° C in a yield of 82%. Analysis, calculated for $C_{26}H_{26}O_6N_2$: C,67.52; H,5.67; N,6.06; found C,67.17, H,5.69; N,5.95.

EXAMPLE 55

In 100 ml of a mixture of chloroform-tetrahydrofuran (2:1), were dissolved 5.39 g of N-benzoylphenylalanine, 4.64 g of methyl tyrosinate hydrochloride, 2.02 g of triethylamine and 2.30 g of N-hydroxysuccinimide and the solution was cooled with ice. To the cold solution, 4.12 g of N,N'-dicyclohexylcarbodiimide was added. The mixture was stirred for 3 hours, then allowed to stand at room temperature overnight. The precipitates were removed by filtration and the filtrate was concentrated. The residue was extracted with ethyl acetate and the extract was washed with 2% hydrochloric acid, 4% sodium bicarbonate and water, then dried and concentrated to dryness. The residue was crystallized from ethyl acetate-petroleum ether to give 6.6 g of methyl N-benzoylphenylalanyl-tyrosinate with a mp. 188°–190° C in a yield of 74%. Analysis, calculated for $C_{26}H_{26}O_5N_2$: C,69.94; H,5.87; N,6.27; found C,69.56; H,6.01; N,6.39.

This ester was hydrolyzed by the same manner as in Example 53 to give N-benzoylphenylalanyltyrosine.

EXAMPLE 56

In 500 ml of a mixture of chloroform-tetrahydrofuran (2:1), were dissolved 29.9 g of N-(4-methoxybenzoyl)-phenylalanine, 23.2 g of methyl tyrosinate hydrochloride, 10.1 g of trethylamine and 11.6 g of H-hydroxysuccinimide and the mixture was cooled with ice. To the cold solution was added 20.6 g of N,N'-dicyclohexylcarbodiimide. The mixture was stirred for 2 hours and then allowed to sit at room temperature overnight. The precipitates were removed by filtration and the filtrate was concentrated. The residue was extracted with ethyl acetate. The extract was washed with 2% hydrochloric acid, 4% sodium bicarbonate and water, then dried and concentrated to dryness. The residue was crystallized from ethyl acetate to give 35 g of methyl N-(4-methoxybenzoyl)-phenylalanyltyrosinate with a mp. 195°–197° C in a yield of 74%. Analysis, calculated for $C_{27}H_{28}O_6N_2$: C,68.05: H,5.92; N,5.88; found C,67.84; H,5.92; N,5.57.

This ester may be hydrolyzed by the same manner as in Example 54 to give N-(4-methoxybenzoyl)-phenylalanyltyrosine.

EXAMPLE 57

To a solution of 10 g of N-(4-methoxybenzoyl)-phenylananine and 100 ml of tetrahydrofuran was added 3.4 g of N-methoylmorpholine. To the mixture, 4.6 g of isobutyl chlorocarbonate was added while stirring at −15° C. The mixture was stirred for 30 minutes and then 100 ml of a mixture of 7.8 g of methyl tyrosinate hydrochloride, 3.4 g of triethylamine and 100 ml of chloroform were added. The resulting mixture was stirred at −10° C for 2 hours and at room temperature for 3 hours. The precipitates were removed by filtration and the filtrate was concentrated and extracted with ethyl acetate. The extract was washed with 2% hydrochloric acid, 4% sodium bicarbonate and water, then dried and concentrated to dryness. The residue was crystallized from ethyl acetate to give 9.9 g of methyl N-(4-methoxybenzoyl)-phenylalanyltyrosinate with mp. 195°–197° C in a yield of 62%. Analysis, calculated for $C_{27}H_{28}O_6N_2$: C,68.05; H,5.92; N,5.88; found C, 68.34; H,5.77; N,5.91.

This ester may be hydrolyzed by the same manner as in Example 54 to give N-(4-methoxybenzoyl)-phenylananyltyrosine.

EXAMPLE 58

In a mixture of 10 ml of water and 50 ml of chloroform were suspended 3.79 g of methyl phenylalanyl-tyrosinate hydrochloride and 0.53 g of sodium carbonate. To the mixture was added dropwise 1.75 g of 4-methoxybenzoylchloride in parallel with 10 ml of sodium carbonate solution (0.75 g), while stirring and cooling with ice. The mixture was stirred for 2 hours and the chloroform layer was collected. The layer was washed with 5% hydrochloric acid and water, dried and concentrated to dryness. The residue was crystallized from ethyl acetate to give 3.9 g of methyl N-(4-methoxybenzoyl)-phenylalanyltyrosinate with a mp. 195°–197° C in a yield of 82%. Analysis, calculated for $C_{27}H_{28}O_6N_2$: C,68.05; H,5.92; N,5.88; found C,68.42; H,6.08; N,5.74.

The ester was hydrolyzed by the same manner as in Example 54 to give N-(4-methoxybenzoyl)-phenylalanyltyrosine.

EXAMPLE 59

In 20 ml of 1N sodium hydroxide solution, 3.28 g of phenylalanyltyrosine was dissolved and the solution was cooled with ice. To the cold solution were added dropwise 1.7 g of 4-methoxybenzoylchloride and 10 ml of 1N sodium hydroxide solution. After stirring for 2 hours, the mixture was neutralized with hydrochloric acid and extracted with ethyl acetate. The extract was washed with water, dried and concentrated to dryness. The residue was crystallized from ethyl acetate to give 2.6 g of N-(4-methoxybenzoyl)-phenylalanyltyrosine in a yield of 56%.

EXAMPLE 60

To a solution of 0.9 g of N-(4-methoxybenzoyl)-phenylalanyltyrosine and 10 ml of ethanol, 10 ml of water was added. The mixture was adjusted to a pH of 8 with 1N sodium hydroxide and concentrated to dryness. Sodium N-(4-methoxybenzoyl)-phenylalanyltyrosinate in the form of a powder was obtained.

EXAMPLE 61

In 400 ml of a mixture of water-isopropanol (1:1), 20 g of N-benzoylphenylalanyltyrosine was dissolved and the solution was warmed to 40° C. To the solution was added 200 ml of isopropanol solution containing 18.8 g of aluminium isopropoxide with stirring. After stirring at 40° C for 1 hour, the mixture was allowed to stand overnight, then centrifuged. The supernatant fluid was concentrated and the residue was dissolved in isopropanol. The solution was centrifuged and the supernatant fluid was concentrated to dryness. The residue was dissolved in isopropanol. To this, water was added to precipitate 10 g of aluminium N-benzoylphenylalanyltyrosine in the form of a powder with mp. 287° C (decomposed).

EXAMPLE 62

In a mixture of 80 ml of ethanol and 30 ml of pyridine, 6.54 g of methyl N-(3,4-dimethoxybenzyloxycarbonyl)-tyrosinate was dissolved. To the solution, 4.41 g of calcium chloride dihydrate was added. Then, to the mixture, 2.27 g of sodium borohydride was slowly added while stirring at room temperature. The resulting mixture was stirred for 3 hours and neutralized with 3% hydrochloric acid. After addition of 250 ml of water, the reaction mixture was concentrated in vacuo and the residue was extracted with ethyl acetate. The extract was washed with water, dried and concentrated to dryness. The residue was crystallized from ethyl acetate to give 3.82 g of N-(3,4-dimethoxy-benzyloxycarbonyl)-tyrosinol. The crystals were recrystallized from ethanol to give small needles with mp. 152°–155° C. Analysis, calculated for $C_{19}H_{23}NO_6$: C,63.14; H,6.42; N,3.88; found C,63.30; H,6.29; N,3.99.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A compound of the formula

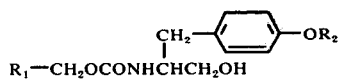

wherein $R_1$ is cyclopentyl, cyclohexyl, cycloheptyl or phenyl, wherein the phenyl may have one or more substituents selected from the group consisting of lower alkyl, lower alkoxy, halogen, amino, nitro and combinations thereof; $R_2$ is hydrogen or lower alkyl; and when $R_1$ is unsubstituted phenyl, $R_2$ is lower alkyl.

2. The compound of claim 1 which is N-(4-methoxybenzyloxy-carbonyl) tyrosinol.

3. The compound of claim 1 which is N-cyclohexylmethoxycarbonyltyrosinol.

4. The compound of claim 1 which is N-(4-methylbenzyloxycarbonyl) tyrosinol.

5. The method of treating ulcers in humans which comprises administering a compound of claim 1 in an amount effective for treating said ulcers.

* * * * *